United States Patent [19]

Lando

[11] Patent Number: 5,347,041

[45] Date of Patent: Sep. 13, 1994

[54] MOLECULAR COMPOSITES

[75] Inventor: Jerome B. Lando, Shaker Heights, Ohio

[73] Assignee: Edison Polymer Innovation Corporation, Brecksville, Ohio

[21] Appl. No.: 78,537

[22] Filed: Jun. 16, 1993

[51] Int. Cl.$^5$ .......................................... C07C 69/017
[52] U.S. Cl. .................... 560/141; 560/138; 560/140
[58] Field of Search .............. 560/205, 221, 138, 141, 560/140

[56] References Cited

PUBLICATIONS

Journal of Organic Chem USSR; Kolotilo 27(7) pp. 1223–1226, 1991.

*Primary Examiner*—José G. Dees
*Assistant Examiner*—Samuel Barts
*Attorney, Agent, or Firm*—Hudak & Shunk Co.

[57] ABSTRACT

Monomers containing two diacetylene segments each of which is connected on one end through a spacer segment to a central mesogen segment, and on the other end to an additional spacer segment, are topochemically polymerized in a molecularly ordered phase to produce homogeneous molecular composites. A preferred monomer embodiment comprises a compound of the formula $$H-(CH_2)_m-C\equiv C-C\equiv C-(CH_2)_n-CO-O-R_1-O-CO-(CH_2)_n-C\equiv C-C\equiv C-(CH_2)_mH$$

where m and n are the number of repeating units, and $R_1$ is a biphenylene mesogen.

2 Claims, No Drawings

MOLECULAR COMPOSITES

TECHNICAL FIELD

This invention relates to homogenous molecular composite structures that exhibit desirable physical properties. More particularly, this invention relates to molecular composite structures formed from unsaturated liquid crystalline and crystalline materials that can be topochemically polymerized in their solid state. Specifically, this invention relates to segmented, rigid-rod molecular composites prepared from mesogen-containing alkyne monomers that are readily polymerized to yield desired composite structures by exposure to radiation or heat.

BACKGROUND OF THE INVENTION

The synthesis of molecular composites, that is composites formed from molecules comprised of stiff or rigid molecular segments, interspersed with flexible segments, has attracted considerable attention in the recent past. In this regard, the reinforcing fibers contained in ordinary composites suffer from the fact that they have a tendency to separate from the material in which they are incorporated, thereby impairing the composites' physical properties. In addition, a substantially homogeneous dispersion of fibers in a composite matrix is frequently difficult to achieve. Partly as a consequence of the foregoing, therefore, there have been many attempts to develop so-called "molecular composites," using techniques designed to overcome the disadvantages described.

Unfortunately, however, molecular composites as they are presently understood might be more accurately described as an objective desirable to achieve, rather than one already accomplished. In this regard, true molecular composites, i.e., composites in which molecular segments are homogeneously distributed in flexible matrix molecular segments are difficult to prepare. This is in consequence of the fact that such rigid segments or "rods" tend to aggregate after reaching a critical concentration. Such aggregates are, in fact, to be expected, being predicted by Flory's theory, Polymer 28, 21–30 (1987). In any event, the heterogeneity commonly experienced significantly impairs the structural reinforcement that molecular composites are designed to provide.

A further problem heretofore experienced with molecular composites arises from the fact that due to their tendency to form domains of concentrated rigid-rod structures, the composites tend to resist thermal processing, making their fabrication into commercial products difficult to achieve.

In the past, a number of techniques have been proposed in order to overcome the difficulties described. For example, it has been suggested that molecules with rods less rigid be used; that matrix molecules having a more flexible character be employed, or both. Where these expedients are resorted to, however, the products obtained frequently prove to have less than desirable physical properties.

A different approach suggested involves fixing the position of the rigid-rod molecules within the matrix molecules, for example, by first dissolving the rigid-rod-containing molecules in a solution of a thermosetting material intended to form the matrix. The mixture is then subjected to curing conditions, thereby causing the dispersed rods to be immobilized within the resulting crosslinked matrix. While homogeneity is achieved, however, the resulting products possess the physical characteristics of the thermoset resin employed, and for that reason, the composites are not always suitable for the end-use required of them.

Still another technique proposed involves the formation of the rigid rods only after a homogeneous mixture of the rods and matrix has been achieved. In this method, coil-like molecules are combined with the matrix material, and following mixing of the two, the mixture is processed to form the desired product. Thereafter, the coil-like molecules are chemically altered to provide the rigid-rods necessary to reinforce the composite. Such in-situ methods, however, present certain problems relating to molecular dynamics, and are to that extent undesirable.

In an effort to prepare useful molecular composites, and at the same time overcome the problems described, attempts have also been made to synthesize molecules that combine both rigid-rod segments and flexible matrix segments within the same molecule. In connection with this approach, resort has been had to the preparation of block copolymers characterized by possessing rigid-rod reinforcing blocks in combination with flexible matrix blocks. In addition, flexible matrix-forming polymer side chains have been grafted onto polymer backbones that include rigid-rod reinforcing segments. Even with these systems, however, one is still confronted with molecular mobility sufficient to cause phase separation of the composites, resulting in the formation of discrete domains of concentrated rigid-rod segments, and portions of the composites in which the matrix segments predominate. Such separation is due to the basic incompatibility of these segments, and thus far undesirable separations of the type described have been difficult to avoid.

BRIEF DESCRIPTION OF THE INVENTION

In view of the foregoing, therefore, it is a first aspect of this invention to provide molecular composites having improved physical properties.

A second aspect of this invention is to provide a monomer suitable for preparing molecular composites that include rigid-rod reinforcing segments and flexible matrix segments in the same molecule.

Another aspect of this invention is to provide molecular composites in which rigid-rod reinforcing segments of the polymers forming the composites are homogeneously distributed within the composites.

An additional aspect of this invention is to provide crystalline or liquid crystalline monomers that can be topochemically polymerized in the solid state.

A further aspect of this invention is to provide crystalline or liquid crystalline monomers that can be polymerized thermally or with radiation to form molecular composites.

Yet another aspect of this invention is to provide acetylenically unsaturated monomers that can be fabricated into a desired product and thereafter polymerized to transform the monomers into a molecular composite.

A still further aspect of this invention is to provide composite structures that are useful in applications where it is desirable to provide a visual record of the forces which the structures have experienced.

The preceding and other aspects of the invention are provided by a compound having the formula:

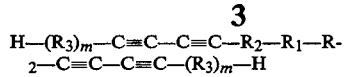

in which $R_1$ comprises a mesogenic group; $R_2$ is a member selected from the group consisting of acyloxy, carboxylate, alkoxy and alkylamide; $R_3$ is alkyl, and m is a whole number from about 3 to 18.

The preceding and further aspects of the invention are provided by a compound having the formula:

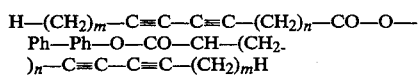

where m is whole number from 3 to 18, and n is a whole number from 2 to 12.

The preceding and additional aspects of the invention are provided by a process for preparing a molecular composite comprising exposing to radiation or heat, a molecularly ordered phase of a compound having a formula according to that set forth in the penultimate paragraph and continuing said exposure for a time sufficient to form a homopolymer from the compound having a desired molecular weight.

The preceding and yet other aspects of the invention are provided by a molecular composite formed by the process of the preceding paragraph.

DETAILED DESCRIPTION OF THE INVENTION

The invention disclosed herein is concerned with the preparation of monomers containing mesogenic groups, spacer groups, and acetylenic groups and their subsequent topochemical polymerization. The monomer compounds disclosed are capable of ordering themselves in either liquid crystalline or crystalline phases, forms in which they readily undergo topochemical, solid state polymerization, that can be initiated by either radiation or heat energy. The resulting polymers are nearly defect-free, extended-chain, single crystal polymers in which the mesogenic groups and the spacer groups act as a composite "matrix," while the polydiacetylene chains function as rigid molecular "fibers." In the resulting composites, the mesogenic and spacer groups supply desirable flexibility and impact resistance, while the polydiacelylene chains formed have a very high measured tensile strength and modulus, therefore supplying good mechanical properties. The resulting composite systems are truly homogeneous since the molecular fibers are dispersed at a molecular level, the composite consisting of a single component system. Inasmuch as the polymerized diacteylene moieties are obtained through topochemical reaction of the liquid crystalline or crystalline monomers, good molecular packing is obtained without the phase separation which separate fiber and matrix components typically experience in conventional multi-component, molecular composite systems.

The diacetylenes of the invention are soluble in common solvents and may be processed from solution or from a melted phase and then polymerized to form the desired composite product. The presence of the mesogenic groups is important since diacetylenes do not polymerize in the isotropic phase, and the presence of such groups allows sufficient order to be realized and maintained to permit the diacetylene groups to undergo topochemical polymerization in the liquid crystalline or crystalline state.

Compounds of the invention have the general formula:

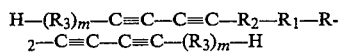

in which $R_1$ includes a mesogenic group, while $R_2$ is an acyloxy, carboxylate, alkoxy or an alkylamide and $R_3$ is alkyl, and in which m is a whole number from about 3 to 18.

Such compounds may be synthesized by methods well known in the art of which the following is an example of a useful synthesis method for preparing 4,4'-bis(10,12-uncosadiynoate)biphenyl, 88 DABP, monomer.

First 1-iodoacetylene is prepared by means of a Grignard reaction in which 1-decyne is reacted with ethylmagnesium bromide in dried ether, and subsequently with iodine, according to the following reaction:

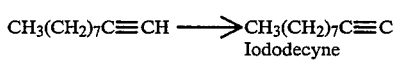

Next, the iododecyne may be unsymmetrically coupled with 10-undecynoic acid with a modified Cadiot-Chodkiewicz coupling reaction to yield the intermediate product 10,12-uncosadiynoic as follows:

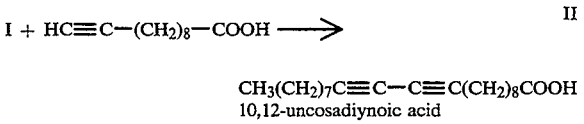

Finally, the 10,12-uncosadiynoic acid is converted to its corresponding acid chloride and reacted with 4,4'-dihydroxybiphenyl in the presence of triethylamine to produce the desired 4,4'-bis(10,12-uncosadiynoate)-biphenyl, as shown in the following reaction:

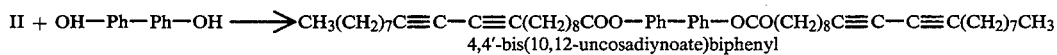

Similar or different methods well known in the art may also be employed to prepare the above and similar compounds.

With respect to the mesogenic group, $R_1$ in the general formula shown in the preceding, such groups may include a wide variety of mesogens including the following.

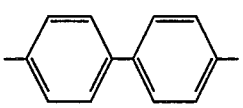  biphenylene

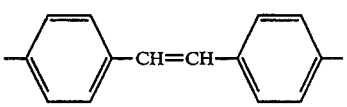  stilbene

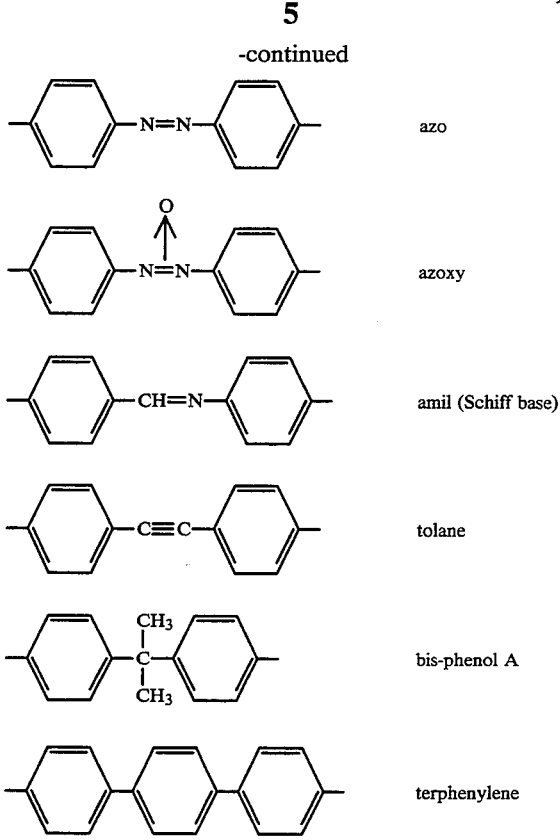

| | |
|---|---|
| (structure) | azo |
| (structure) | azoxy |
| (structure) | amil (Schiff base) |
| (structure) | tolane |
| (structure) | bis-phenol A |
| (structure) | terphenylene |

Of the above, acyloxy constitutes a preferred embodiment of an innerspacers of the invention. n of the innerspacer can be a whole number from about 2 to 12; however, spacer groups in which n is 2, 4 or 8 especially lend themselves to synthesis of monomers of the invention.

While a variety of groups are suitable for use as outer spacers in the monomers, alkyl groups are preferred, with methylene groups being especially preferred. Referring again to the general formula described in connection with the preceding, it has been found that m can be a whole number from about 3 to 18, although certain advantages are realized where the spacer comprises 8 methylene groups.

As previously indicated, the presence of the mesogenic groups permits highly ordered liquid crystalline phases or crystalline phases to be readily achieved. While, as stated in the preceding, diacetylenes cannot be polymerized in the isotropic phase, they can readily be polymerized in the liquid crystalline or crystalline state following the ordering promoted by the presence of the mesogenic groups described. For example, in connection with 4,4'-bis(10,12 uncosadiynoate)biphenyl referred to, it appears that there may be as many as three ordered states, i.e., a first smectic phase reached at from about 82° to 90° C., a second smectic phase apparently present at from about 63° to 72° C., and a three-dimensional crystalline phase obtainable at from about 46° to 51° C. Determination of the ordered phases can readily be accomplished by use of such well-known techniques as differential scanning calorimetry, and other equivalent techniques.

The monomers can readily be processed from solution since they are soluble in a wide variety of solvents such as methylene chloride, chloroform, tetrahydrofuran, acetone, diethylether, and the like. However, the monomers can also be processed from a melt phase. In either case, the possibility of processing the monomer into a desired form prior to its polymerization constitutes a significant advantage of the invention.

It has been found that polymerization of the monomers is readily initiated by radiation, for example, by exposure to ultraviolet or gamma radiation, by exposure to a red laser beam, or by equivalent radiation. During the exposure, a color change is observed, e.g., from white to blue, as a consequence of the conjugated polydiacetylene backbone formed as radiation continues and the polymerization progresses. Continued radiation causes the color to change further, i.e., from blue to dark purple, and finally to dark brown as a consequence of the fact that the increased exposure results in a longer conjugated length of the polydiacetylene chain. Consequently, color change can be used as a guide to molecular weight progression during the polymerization.

The characteristic color change, which can be related to molecular weight by empirical experience, also permits polymers formed from the monomers of the invention to be fashioned into articles useful in monitoring the force to which the articles have previously been exposed. In this regard, as the force to which a sample of the polymer is exposed increases, the polydiacetylene backbone undergoes chain rupture causing corresponding changes in the color of the material. Consequently, visual observation of the material's color provides an indication of the force to which the polymer has been exposed.

In regard to molecular weight, it has been determined that polymerizations of the monomers which progress to a point where the polymer attains a molecular weight of at least about 7,000, $M_n$, provide a particularly preferred embodiment of the invention.

While radiation exposure is a useful way in which to conduct the desired polymerizations, heat may also be employed, and in this regard, polymerization will commonly procede at no more than room temperature within a period of about 4 to 5 hours. In view of this fact, it is desirable to store the monomer in the solution phase, for example, as a chloroform solution, recrystallizing the monomer, for instance with diethylether prior to use. In the case of radiation exposure, polymerization is much more rapid, with a color change becoming apparent in as little as about 1 second in the case of UV light having a wave length of 254 nm.

While not intended to be limiting in nature, the following example is illustrative of the invention.

EXAMPLE 1

Preparation of materials 1-decyne, ethylmagnesium bromide, iodine, copper-(I)chloride, 70% ethylamine, hydroxylamine hydrochloride (HAH), and 4,4'-dihydroxy biphenyl are obtained from Aldrich Chemical Co., Inc. and used as received. 10-undecynoic acid is obtained from Lancaster Synthesis and also used as received. Dried diethylether and dried tetrahydrofuran are prepared by refluxing the solvent over lithium aluminum hydride overnight, and are freshly distilled before use. Thionylchloride and triethyl amine are redistilled prior to use. All other reagents are usea as received unless otherwise specified.

Monomer Synthesis

1-Iododecyne

To a 500 ml 3-neck round bottom flask is transferred an ethylmagnesium bromide solution, 100 ml of 3.0M in dried ether, 0.30 mole, under an argon atmosphere. The contents are cooled to about 0° to 3° C. in a solution of 1-decyne, 25 grams, 0.1808 mole, and 50 ml of dried ether are added dropwise into the reaction mixture over a period of 1.5 hours. Thereafter the mixture is warmed to 35°-38° C. and maintained at that temperature for an additional hour. The mixture is then cooled to about 15° C. and powdered iodine, 80 g., 0.315 mole, is slowly added through a solid addition funnel over a period of about 1.5 hours. The reaction is maintained at 30° C. for approximately 2.5 additional hours. In the meantime, an additional 150 ml of dried ether is added to limit the viscosity increase during the reaction. In the work-up process, 200-300 ml of ether are added and the contents hydrolyzed by slowly pouring them into two liters of cold, dilute acetic acid having a pH of about 1-2. The organic phase is extracted with ether and washed several times with 10 percent $Na_2S_2O_3$ solution to remove the unreacted iodine. Washing continues until the organic phase exhibits a clear color. Following this, the phase is washed several times with water and dried over $MgSO_4$. The solvent is removed by means of a rotary evaporator, and the oily crude product is purified by column chromatography, using silica gel absorbent and hexane as an eluent. The yield is about 90 percent based on 1-decyne used, of a pale yellow liquid, 43.0 grams, 0.1629 mole.

Uncosa-10,12-diynoic acid

To a solution of 10-undecynoic acid, 5.490 grams, 0.03 mole, in 20 ml of 10 percent KOH, are added 400 mg of HAH and Cu(I)Cl solution, 700 mg of Cu(I)Cl in 6.0 grams of 70 percent ethylamine under an argon gas purge. The contents are cooled to about 15° C. and a solution of iododecine, 8.03 grams, 0.03 mole, in 15 ml of tetrahydrofuran are added dropwise to the solution mixture over a period of about ½ hour. The reaction mixture is allowed to proceed at about 20° C. for approximately 0.5 hours, and then acidified with 2N $H_2SO_4$ to a pH of about 1-2. The organic phase is extracted with ether, washed with acidified water, dilute sulphuric acid, pH about 2, in water before being dried over $MgSO_4$. Following the ether treatment, the crude product is rotary-evaporated and purified by recrystallization with petroleum ether, boiling point about 40°-60° C., and subsequently with mixed solvent comprising methanol/water. It is then dried in a vacuum oven at room temperature overnight. A yield of about 3.40 grams, 35 percent, is obtained of the white crystals of uncosa-10,12-diynoic acid having a melting point of about 49.5° to 50° C.

Of the above mesogenic groups, however, biphenylene constitutes a preferred embodiment of the invention.

The mesogenic groups referred to permit the molecular ordering of the monomers of the invention, making topochemical polymerizations in the semi-crystalline or crystalline state possible. The mesogen groups also contribute to the flexibility of the composites, however, with the inner and outer groups, $R_2$ and $R_3$, respectively, also contributing to their flexibility.

The innerspacers, $R_2$, may be selected from any of a number of groups which include one end adapted for connecting the spacer to a phenyl group in the mesogen, and which have an alkyl group on the other end adapted for connecting the spacer to an acetylenic group forming part of the monomer. Among useful innerspacers are groups having the following formulas in which the group is shown in brackets, one end of the group being connected to a phenyl group of the mesogen, and the other end being connected to an acetylenic group, not shown.

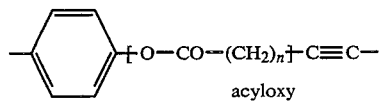
acyloxy

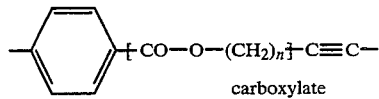
carboxylate

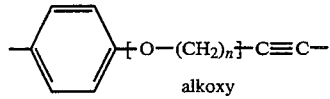
alkoxy

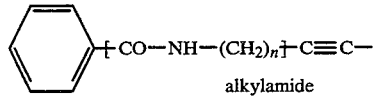
alkylamide

4,4'-bis(uncosadiynoate)biphenyl

Into a dried, 3-neck round-bottom flask equipped with condenser, and maintained under an argon purge are transferred 1.82 grams, 0.006 moles, of uncosa-10,12-diynoic acid, and an excess amount of thionyl chloride, 19.3 grams, 0.162 moles, the latter functioning both as a solvent and as a reagent. The contents of the flask are heated to about 45° C. and maintained at that temperature for approximately 5 hours. A reddish brown solution of the corresponding acid chloride of cosa-10,12-diynoic acid is obtained. The excess amount of thionyl chloride is removed by vacuum evaporation at about 40° C. over a period of approximately 1.5 hours. The contents are then cooled with ice. Following the procedure described, approximately 15 ml of dried tetrahydrofuran are added to dissolve the acid chloride, and a solution of 4,4'-dihydroxy biphenyl, 0.500 grams, 0.10027 moles, in 25 ml of dried tetrahydrofuran are added dropwise into the acid chloride solution over a period of about 25 minutes. The reaction is then allowed to proceed at 20° C. for an additional 4 hours. The organic phase is extracted with dichloromethane, washed several times with water and dried over $MgSO_4$. The solvent is rotary-evaporated and the crude product obtained is purified by double recrystallization from warm ether to obtain 4,4'-bis(uncosadiynoate)biphenyl as a colorless, prism crystal or white powder. The yield is 0.80 grams, 38 percent, based on the 3,3'-dihydroxybiphenyl used.

Polymerization of the Monomer

The 4,4'-bis(uncosadiynoate)biphenyl is polymerized by exposing the powdered material to 20 Mrad of $^{60}Co$ γ-radiation at room temperature, the dose rate being about 26.8 krad/hr. The residual monomer and oligomer in the polymer are washed away with chloroform and the sample is dried in a vacuum desiccator.

EXAMPLE 2

In an additional procedure, a further monomer of the invention having the formula:

H(CH$_2$)$_m$C≡C—C≡C(CH$_2$)$_n$—O—Ph—Ph—O—(CH$_2$)$_n$C≡C—C≡C(CH$_2$)$_m$H is prepared by means of the following steps:

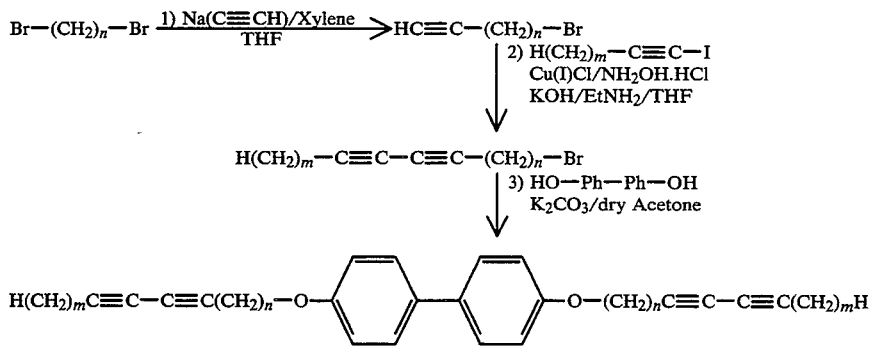

While in accordance with the Patent Statutes, a preferred embodiment and best mode has been presented, the scope of the invention is not limited thereto, but rather is measured by the scope of the attached claims.

What is claimed is:

1. A compound of the formula H—(R$_3$)$_m$—C≡C—C≡C—R$_2$—R$_1$—R$_2$—C≡C—C≡C—(R$_3$)$_m$—H in which R$_1$ is a member selected from the group consisting of

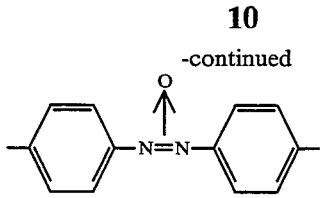

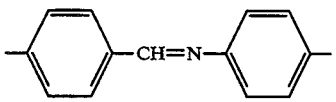

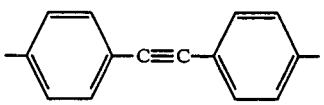

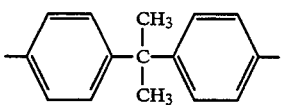

R$_2$ is —O—CO—(CH$_2$)$_n$—; R$_3$ is alkyl, and m is a whole number from about 3 to 18.

2. A compound having the formula H—(CH$_2$)$_m$—C≡C—C≡C—(CH$_2$)$_n$—CO—O—Ph—Ph—O—CO—(CH$_2$)$_n$—C≡C—C≡C—(CH$_2$)$_m$H where m is whole number from 3 to 18, and n is a whole number from 2 to 12.

* * * * *